(12) United States Patent
Viller

(10) Patent No.: US 8,048,148 B2
(45) Date of Patent: Nov. 1, 2011

(54) SELF-EXPANDABLE STENT DELIVERY SYSTEM FOR BIFURCATED LESIONS

(76) Inventor: Alexander G. Viller, Moscow (RU)

( * ) Notice: Subject to any disclaimer, the term of this patent is extended or adjusted under 35 U.S.C. 154(b) by 265 days.

(21) Appl. No.: 12/442,713

(22) PCT Filed: Sep. 25, 2006

(86) PCT No.: PCT/RU2006/000494
§ 371 (c)(1),
(2), (4) Date: Mar. 25, 2009

(87) PCT Pub. No.: WO2008/039090
PCT Pub. Date: Apr. 3, 2008

(65) Prior Publication Data
US 2010/0094389 A1    Apr. 15, 2010

(51) Int. Cl.
*A61F 2/06* (2006.01)
(52) U.S. Cl. .............. 623/1.35; 623/1.11; 623/1.12; 623/1.34; 623/1.37
(58) Field of Classification Search .......... 623/1.34, 623/1.37
See application file for complete search history.

(56) References Cited

U.S. PATENT DOCUMENTS 6,241,758 B1 * 6/2001 Cox .................... 623/1.11
6,464,720 B2 * 10/2002 Boatman et al. ........... 623/1.15

* cited by examiner

*Primary Examiner* — David Isabella
*Assistant Examiner* — Brian Dukert
(74) *Attorney, Agent, or Firm* — Bardmesser Law Group

(57) ABSTRACT

Self-expandable bifurcation stent and systems for delivery and implantation of the self-expandable bifurcation stent, comprising a self-expandable bifurcation stent made of a material possessing shape memory, capable of shaping a mesh with cylindrical surface and marked by radioactive labels, and the delivery system for its implantation, comprising a polymeric tubular catheter with a cap at the distal end, a guiding wire and a pushing wire, where the tubular catheter is executed double-barreled, one lumen accommodating the guiding wire, and the second lumen accommodating the pushing wire with a cap at its distal end, which cap is executed in the shape of a polymeric elastic cap put over the tubular catheter accommodating, between the polymeric elastic cap and the tubular catheter, the stent in the first position with the reduced diameter, the cap is executed with the capability of distal 5 moving along the guiding wire and along the tubular catheter accommodating the stent, by means of the pushing wire, and with capability of unrolling the stent at the proximal end into the second position with greater diameter, and the capability of backwards proximal moving thus returning the stent to its first position in the tubular catheter.

8 Claims, 3 Drawing Sheets

1.1

1.2

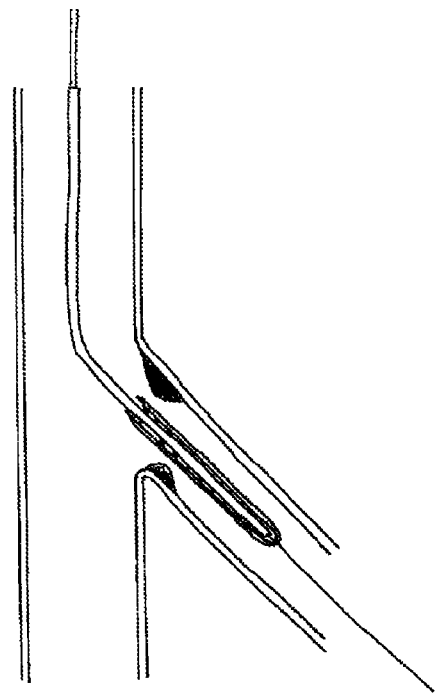
3.1
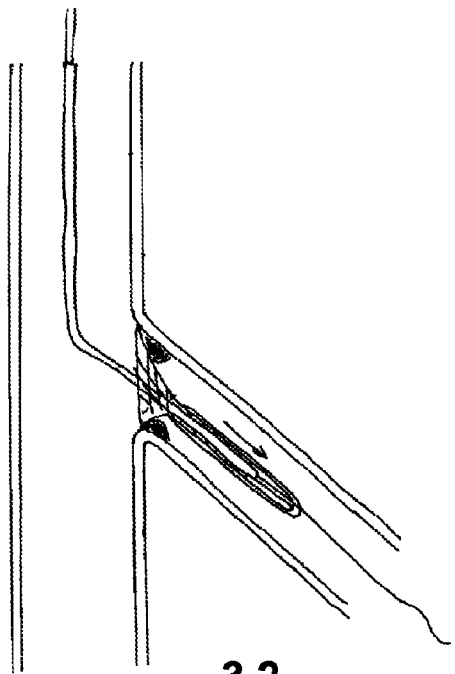
3.2
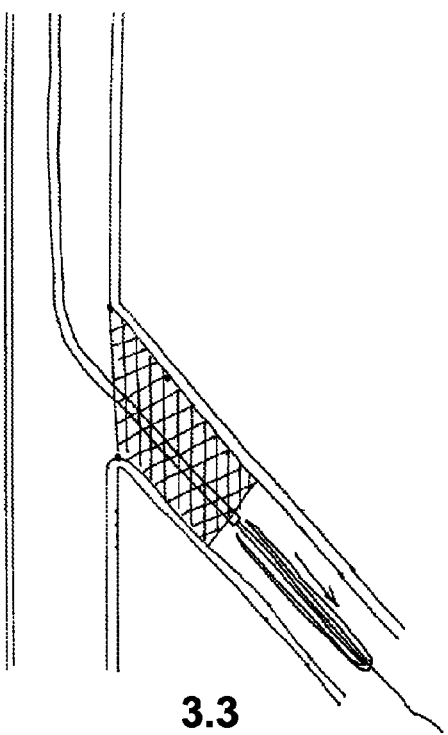
3.3
FIG. 3
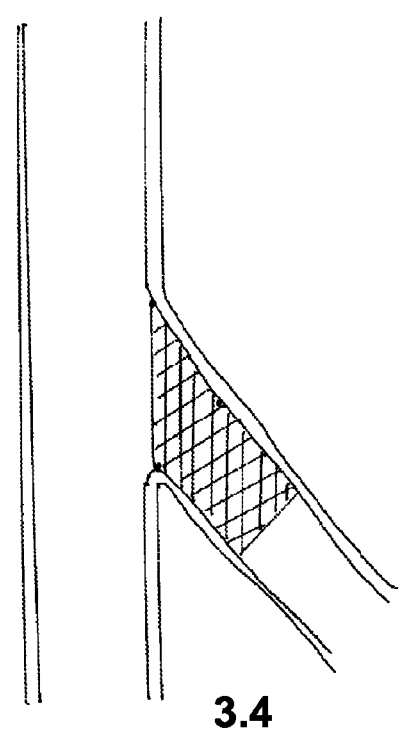
3.4

SELF-EXPANDABLE STENT DELIVERY SYSTEM FOR BIFURCATED LESIONS

CROSS REFERENCE TO RELATED APPLICATIONS

This application is a U.S. National Phase of PCT/RU2006/000494, filed on Sep. 25, 2006, the entire contents of which are hereby incorporated by reference.

BACKGROUND OF THE INVENTION

The invention relates to medical devices, namely to the devices applied in endovascular surgery and interventional cardiology for recovery of narrowed bifurcated sections of a vessel lumen, in particular, in a side branch of the coronary arteries or in the carotid arteries bifurcation.

Fixing a stent in arteries in a bifurcated zone, especially in coronary arteries, constitutes one of the main problems of endovascular surgery and of interventional cardiology in particular. At the present moment, stent techniques, where a stent is implanted into the basic artery are rather common. An additional wire is introduced in a lateral branch through a mesh of the stent and the final angiographic result of the operation is achieved after the balloon angioplasty of the bifurcated zone by two "kissing" balloons. Stenting of bifurcated lesions of arteries is also performed by two stents simultaneously (using techniques: such as cullotte, crush, V-stenting, T-stenting), which represents a high risk of a damage of the arterial wall, a high risk of restenosis and intra-operational technical difficulties. Full optimization of the diameter of an artery in a bifurcated zone by using conventional stents is a difficult problem. There are some designs of special bifurcation stents (for example, the Multi-Link Frontier Stent from Guidant) where the technical result is achieved due to two balloons and two wires on which the stents are clipped and which are positioned both in the basic artery and in a lateral branch. Another type of bifurcation stents has a special mesh structure which has the aperture for a lateral branch (SLK-View™ stent, Advanced Stent Technologies), that allows optimizing implantation of the second stent in a lateral branch. In clinical practice, a Nitinol bifurcation stent by AXXESS Plus, Devax, Inc. is commonly used. The stent is designed in the shape of a frustum, thus, the basic advantage of this stent is the lower probability of shifting plaque masses in a lateral branch during stenting the basic artery. At the same time, all bifurcation stents used today in the clinical practice, have design which, to certain extent, ensures stenting the basic artery and reinforcement of an ostium of a lateral branch, but they do not provide full covering along a lateral branch. These stents have, as a rule, a rather complicated design and the restricted spectrum of application.

From the Russian Patent RU2192810, a set of tools for transluminal insertion of a tubular stent, including self-expandable tubular stent which serves as a transplant, and a device for introduction of the stent, are known. The tool set does not solve the problem of high precision installation of the stent in an ostium of a lateral arterial branch.

An eccentric stent for implantation in a lateral arterial branch is known; it is expanded by means of a balloon catheter (see laid open U.S. Patent Publication No. 2004/0186560). The design of the above stent is adapted for implantation in an ostium segment of a lateral branch of a coronary artery. However, the system of radioactive labels used in this design, does not provide for accurate positioning of the truncated part of the stent in the ostium of the arterial segment that can essentially reduce the safety standard of endovascular operations.

Another solution is presented in Russian patent RU2121317. In this solution the self-recovering stent with delivery system for its implantation in the blood vessel, composing an implantation system, including self-expandable bifurcation stent marked by radioactive labels and made of a wire shaping a cylindrical mesh which material has the shape memory, and the delivery system for implantation of the self-expandable bifurcation stent, containing a polymeric tubular catheter with a polymeric cap at the distal end, a guiding wire and a pushing wire, is described. Though this system has the orientation agents in the form of the radioactive labels located on the stent, the extremely close disposition of labels seriously hampers the accurate orientation by the clipped labels.

SUMMARY OF THE INVENTION

The claimed invention is intended at elimination of drawbacks listed above.

The technical result achieved at use of the claimed system and the device, consists in the increased accuracy of positioning of a stent in a place of an arterial bifurcation or nearby such place, due to new design of the stent, having an oblique part, and due to the particular location of radioactive labels, and in providing a possibility of exact adjustment of the position of the stent during its implantation in a bifurcated arterial segment due to new design of the stent delivery system.

The essence of the claimed invention consists in that a self-expandable bifurcation stent is formed in the shape of the constricted mesh made of a material possessing shape memory and forming, at expansion, a cylindrical surface, marked by radioactive labels, where, at the proximal end, the cylindrical surface of the stent is truncated, and the angle between the longitudinal axis of the stent and the plane of the cross-section, is within the range 30° to 70°, and the radioactive labels are placed on the proximal end of the cylindrical surface of the stent, the first label is located at the end of the short element of the cylindrical surface, the second label is located at its longest element, and the third label is located opposite to the first label.

It is preferable, that the stent has been executed of Nitinol.

Besides, the first radioactive label can have diameter exceeding that of the second label or the third labels.

The mesh with the cylindrical surface can be covered, partially or entirely, by a polymer containing a drug.

Also the mesh with the cylindrical surface can be covered, partially or entirely, by a drug.

The self-expandable bifurcation stent delivery system contains a polymeric tubular catheter with a polymeric cap at the distal end, a guiding wire and a pushing wire, wherein the tubular catheter is formed as a double-channel (i.e., having two lumens or channels), one lumen accommodating the guiding wire, and the second lumen accommodating the pushing wire, whose the distal end is attached to a polymeric cap executed in the shape of a polymeric elastic cap put over the tubular catheter, with capability of accommodating a stent in the space between them, i.e., coaxially. The tubular catheter can be formed as a double-channel in a distal part only, while the lumen for the guiding wire should be available along the whole length of the catheter.

The cap is formed with a capability of distal movement along the guiding wire and along the tubular catheter containing the stent inside, by means of the pushing wire.

Also, the cap has been formed with the capability of proximal movement along the tubular catheter by means of the pushing wire, to its initial position.

The lumens (channels) in the tubular catheter for movement of the guiding wire and the pushing wire have a diameter between 0.007 inches to 0.02 inches.

The system for implantation of the self-expandable bifurcation stent contains a self-expandable bifurcation stent made of a material possessing shape memory, capable of shaping a mesh with cylindrical surface and supplied with radioactive labels, and the delivery system for its implantation, containing a polymeric tubular catheter with a cap at the distal end, a guiding wire and a pushing wire. The tubular catheter is formed as a double-channel, one lumen accommodating the guiding wire, and the second lumen accommodating the pushing wire with a polymeric cap at its distal end. The cap is formed in the shape of a polymeric elastic cap put over the tubular catheter with the capability of accommodating, between the tubular catheter and the polymeric cap, the stent in the first position, i.e., with the reduced diameter, the cap is formed with the capability of distal moving along the guiding wire and along the tubular catheter accommodating the stent, by means of the pushing wire, and with capability of unrolling the stent at the proximal end into the second position, i.e., with greater diameter, and the backwards proximal moving with the capability of returning the stent in its first position in the tubular catheter.

BRIEF DESCRIPTION OF THE DRAWINGS

FIG. 3 shows stages of the stent implantation in the ostium of an artery.

DETAILED DESCRIPTION OF THE PREFERRED EMBODIMENTS

Figure 1:
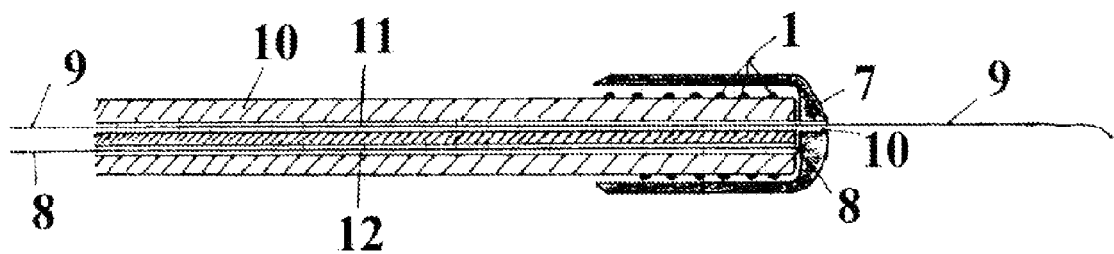
FIG. 1 shows the general view of system for implantation of a self-expandable bifurcation stent.
Figure 1:
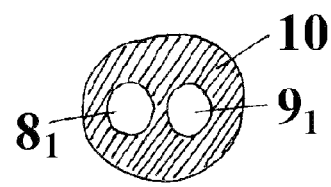
Figure 2:
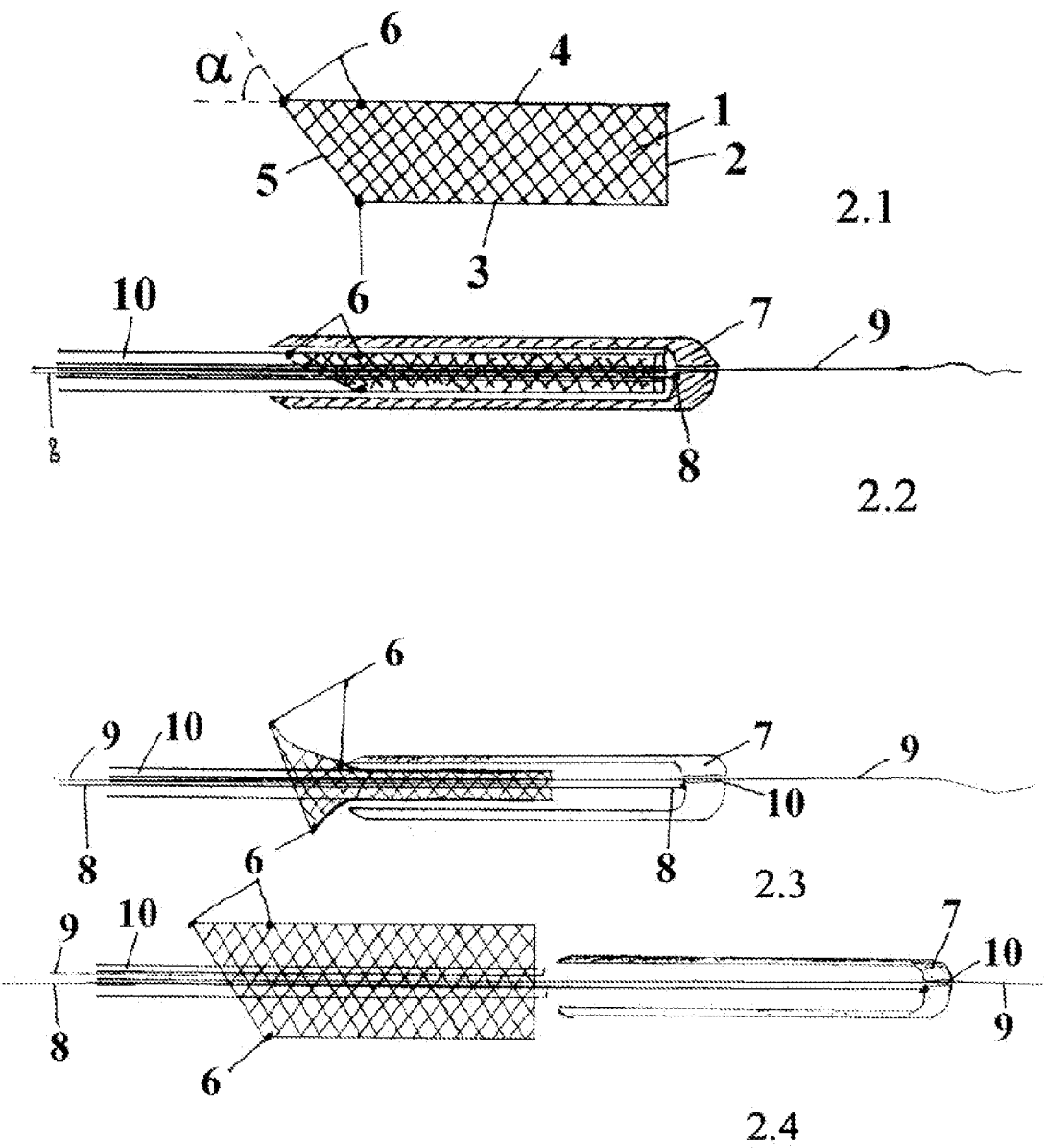
FIG. 2 shows various stages of insertion and remission of a stent at its implantation in the chosen place of a blood vessel.

Self-expandable bifurcation stent 1 (FIG. 1, view 1.1) is made of a material possessing shape memory (for example, Nitinol), capable of shaping a mesh with cylindrical surface. Its cross-section in unrolled, i. e. the second, position, is shown at FIG. 2 (view 2.1), wherein the cylindrical surface of the stent, at the proximal part, is truncated by cross-section 5, and the angle α between the longitudinal axis of the stent and the plane of cross-section 5 is within the range 30° to 70°. The cylindrical surface of the stent contains radioactive labels 6 located at the proximal end of the cylindrical surface of the stent in the mesh points, the first label is located at the end of the short element 3 of the cylindrical surface, the second label is located at the end of the long element 4, and the third label is located on the long element 4 in front of the first label.

The first radioactive label can have the diameter in excess of that of the second or the third labels. Such disposition of labels allows precise positioning of the stent in the ostium segment of an artery during partial shift of a polymeric cap and partial unrolling of a distal part of the stent, and during divergence of labels, is sufficient for precise visualization of the stent position. Also, the mesh with cylindrical surface may be covered, partially or entirely, with a polymer containing drug, or with a drug directly, thus reducing the risk of restenosis in a place of the stent implantation.

The delivery system for implantation of a self-expandable bifurcation stent comprises a polymeric tubular catheter 10 (see FIGS. 1 and 2) with cap 7 at the distal end, a guiding wire 9 and the pushing wire 8, where tubular catheter 10 is formed as a double-channel (see cross-section on FIG. 1, view 1.2), the first lumen 91 of which accommodates guiding wire 9, and the second lumen 81 accommodates pushing wire 8 the distal end of which is affixed to cap 7 executed in the shape of a polymeric elastic cap, put over tubular catheter 10 with the capability of accommodating stent 1 between them, such that in the rolled-up position, the stent 1 is covered entirely by the polymeric cap 7, whose tip is completely closed.

Cap 7 is formed with the capability of distal moving along guiding wire 9 and, accordingly, along tubular catheter 10 accommodating stent 1, by means of pushing wire 8. At the same time, cap 7 is formed with capability of proximal moving along tubular catheter 10 to its initial position by means of pushing wire 8. It is preferable, that the lumens for the guiding wire and the pushing wire in the tubular catheter had the diameter of 0.007 to 0.02 inches.

Delivery system and the bifurcation stent (FIG. 2.1) form a system for implantation of self-expandable bifurcation stent, which works as follows: The guiding wire 9 is introduced into a lateral branch of the basic artery, and along the wire a the self-expandable stent system, i.e., catheter 10, containing stent 1 in the rolled-up position (i.e., with the reduced diameter) (FIG. 2, view 2), is then introduced. By means of pushing wire 8, cap 7 executed in the shape of a polymeric elastic cap and put over tubular catheter 10, is moved to the distal direction along the branch of the vessel (see FIG. 3, view 3.1), along the guiding wire 9 and along tubular catheter 10 (in the first and in the second lumens of the catheter), thus releasing the proximal part of stent 1.

At this stage the proximal part of stent 1 is unrolled in the second position, i.e., with a larger (expanded) diameter (see FIG. 2, view 2.3), and the first and the second radioactive labels 6 should coincide with the proximal end of the stented section (FIG. 3, view 3.2), the third label is located opposite to the first one and, due to larger diameter of the proximal part of stent 1, enables more precise positioning of the stent in the ostium of an artery, for example, by rotating the catheter, the oblique part of which will be thus placed in the correct position.

In case where the exact placement of the stent requires its rotation along the longitudinal axis or movement along the vessel, the cap 7 is moved in the proximal direction, and the stent returns to its first position with the reduced diameter.

After adjustment of the exact position of the stent, the cap 7, by being moved to the distal direction, completely releases the stent (FIG. 2, view 2.4 and FIG. 3, view 3.3), which restores its cylindrical shape with the oblique proximal end in the ostium of the artery, and the cap, together with the catheter, can be removed by moving to proximal direction (FIG. 3, view 3.4).

The claimed design provides for high reliability and precision in installing the stent in an ostium of an artery that essentially reduces procedure risk resulting from the non-optimum implantation of the stent.

What is claimed is:

1. A delivery system for implantation of self-expandable bifurcation stent into a side branch of a bifurcated vessel, the delivery system comprising:
   a polymeric tubular catheter having a polymeric cap at its distal end;
   a guide wire passing through a distal portion of the catheter;
   a pushing wire;
   at least two non-concentric channels formed along the longitudinal axis of the polymeric tubular catheter, the first channel accommodating the guide wire, and the second channel accommodating the pushing wire that has its distal end attached to the polymeric cap;

the polymeric cap formed in a shape that slidably encloses a self-expandable tubular stent which is mounted over the tubular catheter;

wherein the tubular stent has an eccentric proximal end oriented at an angle between a longitudinal axis of the stent and a plane of the cross-section of between 30 degrees and 70 degrees, with a first marker located on a proximal-most portion of the eccentric proximal end, and a second marker located on a distal portion of the eccentric proximal end; and the delivery system adapted to place the stent at the side branch and to move the cap off the stent using the pushing wire, and to rotate the stent while using the first and second markers for locating and rotating the stent so as to match the eccentric proximal end to an opening of the side branch.

2. The system of claim 1, wherein the channel for the pushing wire is formed along an entire length of the catheter.

3. The system of claim 1, wherein the cap is formed with a capability of distal movement along the guide wire and along the tubular catheter having the stent inside, by means of the pushing wire.

4. The system of claim 1, wherein the cap is formed with the capability of proximal movement along the tubular catheter to its initial position by means of the pushing wire.

5. The system of claim 1, wherein the channels in the tubular catheter for movement of the guide wire and the pushing wire have diameters between 0.007 inches to 0.02 inches.

6. A system for implantation of the self-expandable bifurcation stent, comprising:

a self-expandable bifurcation stent made of a material possessing shape memory, capable of shaping a mesh with a cylindrical surface and marked by first and second radio-opaque labels; and a delivery system for implantation of the stent, the delivery system comprising a polymeric tubular catheter with a polymeric cap at the distal end that is slidably mounted over the stent, a guide wire and a pushing wire, wherein the tubular catheter is formed with two non-concentric channels along its longitudinal axis, the first channel accommodating the guide wire, and the second channel accommodating the pushing wire with the cap attached to its distal end, wherein the stent is accommodated between the polymeric elastic cap and the tubular catheter, the stent in a first position with a reduced diameter, and wherein the cap is capable of both distal and proximal movement along the guide wire and along the tubular catheter, by means of the pushing wire, and wherein the cap is capable of unfolding the stent at the proximal end into the second position with greater diameter, and wherein the cap is capable of proximal movement to return the stent to the first position in the tubular catheter, wherein the stent has an eccentric proximal end oriented at an angle between a longitudinal axis of the stent and a plane of the cross-section of between 30 degrees and 70 degrees, with the first radio-opaque marker located on a proximal-most portion of the eccentric proximal end, and the second radio-opaque marker located on a distal portion of the eccentric proximal end; and the delivery system adapted to place the stent at the side branch and to move the cap off the stent using the pushing wire, and to rotate the stent while using the first and second markers for locating and rotating the stent so as to match the eccentric proximal end to an opening of the vessel side branch.

7. The system of claim 6, wherein the first radio-opaque label is larger than the second radio-opaque label so as to enable accurate positioning and orientation of the stent in the side branch using the delivery system.

8. The system of claim 6, wherein further comprising a third radio-opaque label located in a position diametrically opposed to the second label so as to enable accurate positioning and orientation of the stent in the side branch using the delivery system.

* * * * *